| United States Patent [19] | [11] | 4,092,350 |
|---|---|---|
| Miura et al. | [45] | May 30, 1978 |

[54] ALKANOIC ACID, PROCESS FOR ITS PRODUCTION AND METHOD OF USE THEREOF

[75] Inventors: Koji Miura, Kanazawa; Kenjun Takeshima, Nyuzen; Takuya Kodama, Uozu; Masashi Imamura, Toyama; Kyoko Hongo, Toyama; Noboru Takagawa, Toyama; Yukitaka Hamatani, Toyama; Yasuyuki Suzuki, Toyama, all of Japan

[73] Assignee: Toyama Chemical Company Limited, Tokyo, Japan

[21] Appl. No.: 677,092

[22] Filed: Apr. 14, 1976

[30] Foreign Application Priority Data

Apr. 23, 1975  Japan ................... 50-48593

[51] Int. Cl.² .............. C07C 65/02; A61K 31/19
[52] U.S. Cl. ..................... 260/521 R; 260/338; 260/348.58; 260/515 R; 260/590 R; 260/599; 260/340.9 R; 424/317
[58] Field of Search ................... 260/521 R

[56] References Cited

U.S. PATENT DOCUMENTS

| 3,054,779 | 9/1962 | Wheeler | 260/521 R |
| 3,452,079 | 6/1969 | Shen et al. | 260/515 R |
| 3,457,300 | 7/1969 | Dorn et al. | 260/515 R |
| 3,880,916 | 4/1975 | Dickel et al. | 260/521 R |
| 3,888,920 | 6/1975 | Eberle | 260/515 R |
| 3,925,458 | 12/1975 | Kogure et al. | 260/521 R |

OTHER PUBLICATIONS

Houlihan, Chem. Absts., 4001(s), vol. 82, 1975.
Kaiser et al., Chem. Absts., 115595(z), vol. 84, 1976.
Oowaki et al., Chem. Absts., 46208(g), vol. 85, 1976.

Primary Examiner—James O. Thomas, Jr.
Assistant Examiner—G. T. Breitenstein
Attorney, Agent, or Firm—Bierman & Bierman

[57] ABSTRACT

A novel 2-[4-(3-oxo- or hydroxy-alkyl)phenyl]alkanoic acid and a non-toxic salt thereof. These compounds are useful for treating symptoms of inflammation and pain in mammals including man. This disclosure relates to such compounds, a process for producing the same, a pharmaceutical composition containing such a compound, and a method for treating symptoms of inflammation and pain.

8 Claims, No Drawings

ALKANOIC ACID, PROCESS FOR ITS PRODUCTION AND METHOD OF USE THEREOF

This invention relates to a novel 2-[4-(3-oxo- or hydroxy-alkyl)phenyl] alkanoic acid and a non-toxic salt thereof. The invention also relates to a process for producing such compounds, to a pharmaceutical composition containing such a compound, and to a method for treating symptoms of inflammation and pain.

It is an object of the invention to provide a novel compound which is useful as a therapeutic drug for the relief of inflammation and pain in mammals.

It is another object of the invention to provide a novel compound which is useful as a therapeutic drug for the relief of inflammation and pain caused by rheumatism.

We have now discovered that a compound of the general formula (I):

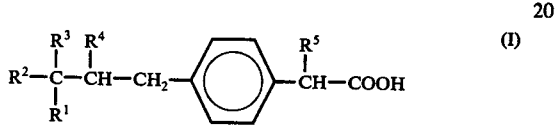

wherein $R^1$ represents a hydrogen atom and $R^2$ represents a hydroxy group, or $R^1$ represents together with $R^2$ an oxo group; $R^3$ represents a lower alkyl group; $R^4$ represents a hydrogen atom or a lower alkyl group; and $R^5$ represents a lower alkyl group, wherein the term lower alkyl for $R^3$–$R^5$ is defined as having 1 – 5 carbon atoms, and a non-toxic salt thereof have valuable anti-inflammatory properties and analgesic properties. The anti-inflammatory properties render the compound useful in treating acute inflammation and subacute inflammation including that caused by rheumatism.

Furthermore, they exhibit a greater degree of safety in anti-inflammatory therapeutic usage when compared with Ibuprofen. In addition, there is shown little undesirable pharmacological activity which might give rise to unwanted side effects.

In general formula (I), $R^5$ is preferably a methyl group. The following compounds are therefore typical of the active compounds of general formula (I), but do not limit the invention in any way.

2-[4-(3-oxobutyl)phenyl]propionic acid,
2-[4-(3-hydroxybutyl)phenyl]propionic acid,
2-[4-(2-methyl-3-oxobutyl)phenyl]propionic acid,
2-[4-(2-methyl-3-hydroxybutyl)phenyl]propionic acid,
2-[4-(2-ethyl-3-oxobutyl)phenyl]propionic acid,
2-[4-(2-ethyl-3-hydroxybutyl)phenyl]propionic acid,
2-[4-(2-propyl-3-oxobutyl)phenyl]propionic acid,
2-[4-(2-propyl-3-hydroxybutyl)phenyl]propionic acid,
2-[4-(2-methyl-3-oxopentyl)phenyl]propionic acid,
2-[4-(2-methyl-3-hydroxypentyl)phenyl]propionic acid,
2-[4-(2-ethyl-3-oxopentyl)phenyl]propionic acid,
2-[4-(2-ethyl-3-hydroxypentyl)phenyl]propionic acid,
2-[4-(2-propyl-3-oxopentyl)phenyl]propionic acid,
2-[4-(2-propyl-3-hydroxypentyl)phenyl]propionic acid,
2-[4-(2-butyl-3-oxopentyl)phenyl]propionic acid,
2-[4-(2-butyl-3-hydroxypentyl)phenyl]propionic acid It is more preferable to have $R^3$ as a methyl group in general formula (I). More particularly, the preferred compounds are 2-[4-(2-methyl-3-hydroxybutyl)-phenyl]propionic acid and 2-[4-(2-ethyl-3-hydroxybutyl)-phenyl]propionic acid.

This invention includes all the stereoisomers within the scope of formula (I).

The non-toxic salts of the compounds of formula (I) are the salts with various well known pharmaceutically acceptable organic or inorganic bases. More particularly, these bases are, for example, alkali metals such as sodium, potassium, etc., alkaline earth metals such as calcium, magnesium, etc., and various basic amino acids. The basic amino acids include D-lysine, L-lysine, DL-lysine, D-hydroxylysine, L-hydroxylysine, DL-hydroxylysine, D-arginine, L-arginine, DL-arginine, D-ornithine, L-ornithine and DL-ornithine.

According to the present invention, it is possible to obtain the compound of formula (I) by oxidizing in the usual manner the aldehyde (IIa) or (IIb) based on the following scheme.

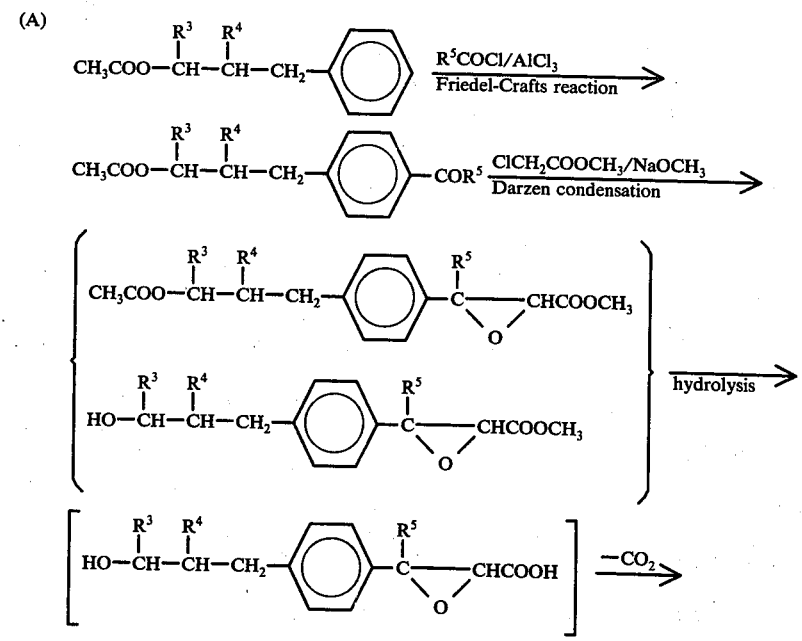

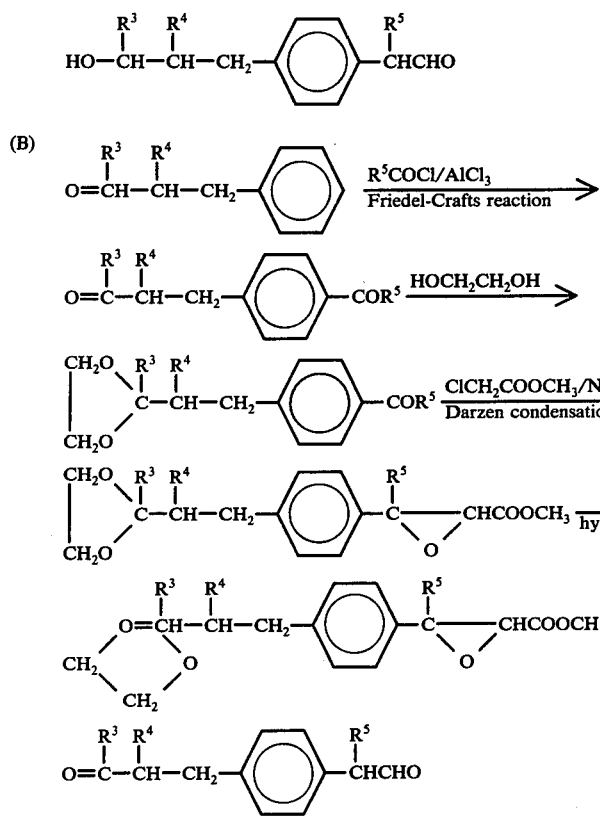

In the scheme, $R^3$, $R^4$ and $R^5$ are the same as defined previously.

Oxidizing agents suitable for preparing the compounds of formula (I) from the aldehyde (IIa) or (IIb) include, for example, hydrogen peroxide, potassium permanganate, potassium dichromate, sodium dichromate, nitric acid, silver oxide, and oxygen in the presence of a catalyst such as silver oxide.

The reactions are carried out in various media suitable to the oxidizing agents and the aldehydes, and the reaction temperature depends on such reactants. If the oxidizing agent is potassium dichromate or sodium dichromate, the aldehyde (IIa), wherein $R^2$ is a hydroxy group, is converted to the compound of formula (I), in which $R^1$ represents together with $R^2$ an oxo group, by oxidation of the hydroxy group.

Furthermore the resulting compounds can be converted to the corresponding non-toxic salts in the usual manner.

Suitable tests for pharmacological activities of the compound of formula (I) are shown below. On the basis of the results, anti-inflammatory activities and acute toxicity in rats are shown in Table 1. The safety margin (the ratios of $LD_{50}$ to $ED_{20}$, to $ED_{30}$, or to $ED_{40}$) for anti-inflammatory activities in rats and analgesic activity in mice are shown in Table 2.

(a) Inhibition of Carrageenin-Induced Paw Edema

Following the method of C. A. Winter, et al. (Proc. Soc. Exp. Biol. Med., 111, 544 (1962)), one hour after the oral administration of the test compounds in male Donryu rats weighing 140 ± 10 g., 0.1 ml. of 1% carrageenin suspension in physiological saline was injected subcutaneously into the plantar side of the right hind paw. The volume of the paw was measured before and 3 hours after the carrageenin injection. The swelling index of the inflamed paw was calculated as follows.

Swelling Index (%) =

$$\frac{\left(\begin{array}{c}\text{Mean Volume of}\\\text{Paw 3 hours}\\\text{after Injection}\end{array}\right) - \left(\begin{array}{c}\text{Mean Volume of}\\\text{Paw before}\\\text{Injection}\end{array}\right)}{\text{Mean volume of Paw before Injection}} \times 100$$

Inhibitory percentage was calculated as follows.

Inhibition (%) =

$$\frac{\left(\begin{array}{c}\text{Swelling Index}\\\text{of Control Rats}\end{array}\right) - \left(\begin{array}{c}\text{Swelling Index}\\\text{of Treated Rats}\end{array}\right)}{\text{Swelling Index of Control Rats}} \times 100$$

(b) Inhibition of Intraperitoneal Dye Leakage

Following the method of B. A. Whittle (Br. J. Pharmac. Chemother., 22, 246 (1964)), one hour after the oral administration of the test compounds in male Donryu rats weighing 160 ± 10 g., 0.5 ml. of 0.5% Evans' blue dissolved in physiological saline was injected intravenously. Five minutes thereafter, 0.2 ml. / 100 g. body weight of 3% acetic acid was injected intraperitoneally. The dye in the peritoneal exudation, sampled 45 minutes after the acetic acid injection, was subjected to the spectro-photometric estimation at 620 m$\mu$. Inhibitory percentage was calculated as follows.

Inhibition (%) =

-continued $$\frac{\left(\begin{array}{c}\text{Mean Optical} -\\ \text{Density of}\\ \text{Control Rats}\end{array}\right) - \left(\begin{array}{c}\text{Mean Optical} -\\ \text{Density of}\\ \text{Treated Rats}\end{array}\right)}{\left(\begin{array}{c}\text{Mean Optical} - \text{Density}\\ \text{of Control Rats}\end{array}\right)} \times 100$$

(c) Inhibition of Granuloma Formation by Gramuloma Pouch Method

Following the method of A. Robert and J. E. Nezamis (Acta. Endocrinol., 25, 105 (1957)), an air pouch of 25 ml. was formed subcutaneously at the back of male Wistar rats weighing 180 ± 10 g., and 1 ml. of 1% croton oil dissolved in cotton seed oil was injected into the pouch. Thereafter, the compounds were administered orally. Beginning the next day, the compounds were administered orally at 9:00 a.m. and 4:00 p.m. for 6 days. The day after final administration, the granuloma pouches were removed and weighed. Inhibitory percentage was calculated as follows:

Inhibition (%) =

$$\frac{\left(\begin{array}{c}\text{Mean Weight of}\\ \text{Granuloma of}\\ \text{Control Rats}\end{array}\right) - \left(\begin{array}{c}\text{Mean Weight of}\\ \text{Granuloma of}\\ \text{Treated Rats}\end{array}\right)}{\left(\begin{array}{c}\text{Mean Weight of Granuloma}\\ \text{of Control Rats}\end{array}\right)} \times 100$$

(d) Acute Toxicity

The compounds were administered orally in male Wistar rats weighing 200 ± 10 g. The rats were observed over a 7-day period.

(e) Inhibition of Granuloma Formation by Cotton Pellet Method

Following the method of C. A. Winter, et al. (J. Pharmac. Exp., Ther., 141, 369 (1963)), in male Donryu rats weighing 130 ± 10 g., two sterilized cotton pellets weighing 35 ± 1 mg. respectively were embedded subcutaneously at the lateral abdomen aseptically. Thereafter, the compounds were administered orally. Beginning the next day, the compounds were administered orally at 9:00 a.m. and 4:00 p.m. for 3 days. The day after final administration, the pellets were removed, dried and weighed to determine the weight of the granuloma formed around the pellets. Inhibitory percentage was calculated as follows:

Inhibition (%) =

$$\frac{\left(\begin{array}{c}\text{Mean Weight of}\\ \text{Granuloma of}\\ \text{Control Rats}\end{array}\right) - \left(\begin{array}{c}\text{Mean Weight of}\\ \text{Granuloma of}\\ \text{Treated Rats}\end{array}\right)}{\left(\begin{array}{c}\text{Mean Weight of Granuloma}\\ \text{of Control Rats}\end{array}\right)} \times 100$$

(f) Analgesic Activity by Acetylcholine-Induced Writhing Method in Mice

Following the method of S. S. Adams (Arch. Int. Pharmacodyn., 178, 115 (1969)), in male SLC-ICR mice weighing 20 ± 1 g., the writhing response was caused by the intraperitoneal injection of 0.1 ml. / 10 g. body weight of 7.5 mg. / kg. acetylcholine dissolved in physiological saline. The test compounds were administered orally 60 minutes before the acetylcholine injection, after which the frequency of response was counted in each animal for 8 minutes. Inhibitory percentage was calculated as follows.

Inhibition (%) =

$$\frac{\left(\begin{array}{c}\text{Mean Frequency}\\ \text{of Response of}\\ \text{Control Mice}\end{array}\right) - \left(\begin{array}{c}\text{Mean Frequency}\\ \text{of Response of}\\ \text{Treated Mice}\end{array}\right)}{\left(\begin{array}{c}\text{Mean Frequency of Response}\\ \text{of Control Mice}\end{array}\right)} \times 100$$

Note;

Compound A: 2-[4-(2-methyl-3-oxobutyl)phenyl]propionic acid,

Compound B: 2-[4-(2-methyl-3-hydroxybutyl)phenyl]propionic acid,

Compound C: 2-[4-(2-ethyl-3-oxobutyl)phenyl]propionic acid,

Compound D: 2-[4-(2-ethyl-3-hydroxybutyl)phenyl]propionic acid

Table 1

| | Anti-Inflammatory Activities and Acute Toxicity in Rats | | | | | | | |
|---|---|---|---|---|---|---|---|---|
| | Effect on Acute Inflammation | | | | Effect on Subacute Inflammation | | | |
| | Inhibition of Carrageenin-Induced Paw Edema | | Inhibition of Intraperitoneal Dye Leakage | | Inhibition of Granuloma Formation by Granuloma Pouch Method | | Acute Toxicity | |
| Compound | Dose (mg/kg) | Inhibition (%) | Dose (mg/kg) | Inhibition (%) | Dose (mg/kg) | Inhibition (%) | Dose (mg/kg) | Died Treated |
| Compound A | 3 | 31.7 | 2 | 30.6 | 8 | 22.3 | 250 | 1/8 |
| Compound B | 3 | 34.9 | 2 | 35.3 | 6 | 24.2 | 250 | 1/8 |
| Compound C | 2 | 35.2 | 0.5 | 28.2 | 1 | 22.7 | 125 | 2/8 |
| Compound D | 2 | 38.1 | 0.5 | 34.4 | 1 | 23.5 | 125 | 3/8 |
| Ibuprofen (reference) | 10 | 31.2 | 10 | 17.8 | 50 | 21.1 | 625 | 3/8 |

Table 2

| | The Safety Margin (the ratios of $LD_{50}$ to $ED_{20}$, to $ED_{30}$, or to $ED_{40}$ for Anti-Inflammatory Activities in Rats and Analgesic Activity in Mice | | | | | | | | | |
|---|---|---|---|---|---|---|---|---|---|---|
| | Effect on Acute Inflammation | | | | Effect on Subacute Inflammation | | | | | Analgesic Activity by Acetylcholine-Induced Writhing Method |
| | Inhibition of Carrageenin-Induced Paw Edema | | Inhibition of Intraperitoneal Dye Leakage | | Inhibition of Granuloma Formation by Granuloma Pouch Method | | Inhibition of Granuloma Formation by Cotton Pellet Method | | Acute Toxicity | |
| Compound | $ED_{40}$ (mg/kg) | $\frac{LD_{50}}{ED_{40}}$ | $ED_{30}$ (mg/kg) | $\frac{LD_{50}}{ED_{30}}$ | $ED_{20}$ (mg/kg) | $\frac{LD_{50}}{ED_{20}}$ | $ED_{20}$ (mg/kg) | $\frac{LD_{50}}{ED_{20}}$ | $LD_{50}$ (mg/kg) | $ED_{50}$ (mg/kg) |
| Compound D | 2.5 | 52.8 | 0.31 | 425.8 | 0.73 | 180.8 | 0.33 | 400.0 | 132 | 2.7 |

Table 2-continued

The Safety Margin (the ratios of $LD_{50}$ to $ED_{20}$, to $ED_{30}$, or to $ED_{40}$ for Anti-Inflammatory Activities in Rats and Analgesic Activity in Mice

| Compound | Effect on Acute Inflammation | | | | Effect on Subacute Inflammation | | | | Acute Toxicity | Analgesic Activity by Acetyl-choline-Induced Writhing Method |
|---|---|---|---|---|---|---|---|---|---|---|
| | Inhibition of Carrageenin-Induced Paw Edema | | Inhibition of Intraperitoneal Dye Leakage | | Inhibition of Granuloma Formation by Granuloma Pouch Method | | Inhibition of Granuloma Formation by Cotton Pellet Method | | | |
| | $ED_{40}$ (mg/kg) | $LD_{50}/ED_{40}$ | $ED_{30}$ (mg/kg) | $LD_{50}/ED_{30}$ | $ED_{20}$ (mg/kg) | $LD_{50}/ED_{20}$ | $ED_{20}$ (mg/kg) | $LD_{50}/ED_{20}$ | $LD_{50}$ (mg/kg) | $ED_{50}$ (mg/kg) |
| Ibuprofen (reference) | 16 | 42.8 | 17 | 40.3 | 42 | 16.3 | 22 | 31.1 | 685 | 4.7 |

From the Tables 1 and 2, it is clear that the novel 2-[4-(3-oxo- or hydroxy-alkyl)phenyl] alkanoic acid of formula (I) has excellent anti-inflammatory and analgesic activities compared with Ibuprofen. In particular, the effect on subacute inflammation is excellent, and the safety margin (the ratio of $LD_{50}$ to $ED_{20}$), which shows the degree of safety, is about 10 times that of Ibuprofen. Therefore, the compound of formula (I) and its non-toxic salt are useful as a therapeutic drug for the relief of inflammation and pain including that caused by rheumatism.

The novel 2-[4-(3-oxo- or hydroxy-alkyl)phenyl]-alkanoic acid of formula (I) and its non-toxic salt may be formulated in the usual way in dosage forms for both oral and parenteral administration, such as capsules, powders, granules, pills, tablets, suspensions, emulsions, syrups, injections, supositories, etc.

The dosage of the active ingredient to be administered varies with the degree of activity of the compound being employed. Generally, dosage levels of 1 to 100 mg. / kg. of body weight are administered to mammals daily to obtain effective relief of inflammation and pain. It is therefore convenient that such dosages include the active ingredient of from 10 to 200 mg. per unit.

More particularly, the formulations are shown below.

(a) In the solid dosage forms such as capsules, powders, granules, pills, tablets, etc., the active compound is admixed with at least one inert diluent such as sucrose, lactose, starch, etc. The dosage forms such as granules, pills, tablets, etc. can also contain additional substances other than inert diluent, for example, binders such as starch solution, gelatin solution, methyl cellulose, microcrystalline cellulose, etc., and disintegrants such as starch, agar-agar, calcium cellulose glycolate, etc. In the case of tablets, the dosage form may also contain lubricants such as magnesium stearate, stearic acid, talc, etc., and can additionally be prepared with enteric coatings, if necessary.

(b) In the liquid dosage forms such as suspensions, emulsions, syrups, etc., the active compound is admixed with liquid vehicles such as water. Such dosage forms can also contain additional substances such as suspending agents, emulsifying agents or thickening agents, as for example, carboxymethyl cellulose, microcrystalline cellulose or tragacanth. Further, the dosage forms may additionally contain, for example, sweetening agents and aromatic substances.

(c) In aqueous or non-aqueous injections, the active compund is admixed with water for injection or with non-aqueous injectable liquid vehicles, for example, vegetable tallow such as olive oil, sesame oil, soybean oil, etc. and organic solvents such as propylene glycol, ethanol, glycerine, polyethylene glycol, etc. Such dosage forms can also contain additional substances, if necessary, for example, stabilizers, solubilizing agents, suspending agents, emulsifying agents, buffering agents and preservatives. They may also be manufactured in the form of sterile solid compositions which can be dissolved in sterile water or some other sterile injectable medium immediately prior to use.

(d) In supositories, the active compound is admixed with well known inert bases such as cacao butter, raurin butter, glycerogelatin, macrogol, etc. If necessary, such dosage forms can also contain additional substances, for example, surfactants and preservatives.

Furthermore, the concrete examples of pharmaceutical compositions are shown below, but these examples do not limit the scope of invention.

1. Tablet
Rp. 2-[4-(2-methyl-3-hydroxybutyl)phenyl]propionic
| | |
|---|---|
| acid | 25.0 mg. |
| Lactose | 56.0 mg. |
| Starch | 37.5 mg. |
| Microcrystalline cellulose | 30.0 mg. |
| Magnesium stearate | 1.5 mg. |
| | 150.0 mg./Tab. |

2. Tablet
Rp. 2-[4-(2-ethyl-3-hydroxybutyl)phenyl]propionic
| | |
|---|---|
| acid | 25.0 mg. |
| Granulated lactose | 69.0 mg. |
| Calcium cellulose glycolate | 5.0 mg. |
| Magnesium stearate | 1.0 mg. |
| | 100.0 mg./Tab. |

These tablets were formulated by the conventional granulation method using aqueous or non-aqueous liquid vehicles containing various binders, or by dry granulation.

Procedures for producing the compounds of formula (I) are shown below with reference to the examples.

EXAMPLE 1

Preparation of 2-[4-(2-methyl-3-hydroxybutyl)phenyl]propionic acid (1) (2-methyl-3-acetoxybutyl)benzene (61.8 g.) was added dropwise to a mixture of acetyl chloride (50 ml.), aluminum chloride (90 g.) and methylene chloride (200 ml.) with stirring below 35° C. over a period of 30 minutes.

After the reaction mixture was stirred at 25° C for 4 hours, it was poured into ice-water, and extracted with methylene chloride. Then the methylene chloride extract was washed with dilute hydrochloric acid, and freed of solvent by evaporation in vacuo. The resulting liquor was fractionated by vacuum distillation to obtain 4-(2-methyl-3-acetoxybutyl)phenyl methyl ketone (60 g.), yield 80%.

b.p. 113° – 117° C / 0.15 mmHg Ir(neat) cm$^{-1}$: $\nu_{C=O}$ 1670 (aromatic ketone) $\nu_{C=O}$ 1720 (ester)

(2) Sodium methoxide was added to a mixture of 4-(2-methyl-3-acetoxybutyl)-phenyl methyl ketone (24.8 g.), methyl chloroacetate (21 g.) and n-hexane (80 ml.) (12 g.) with stirring in a stream of nitrogen at -5° – 0° C over a period of 1 hour. Subsequently, after the reaction temperature was raised to 25° C for 1 hour, the mixture was stirred at 35° – 40° C for 3 hours.

Then the resulting mixture was poured into ice-water and extracted with diethyl ether. The diethyl ether extract was washed with water, dried, and then evaporated in vacuo to obtain a mixture (28.5 g.) consisting of methyl 3-[4-(2-methyl-3-acetoxybutyl)phenyl]-2,3-epoxy butanoate and methyl 3-[4-(2-methyl-3-hydroxybutyl)-phenyl]-2,3-epoxybutanoate.

IR(neat) cm$^{-1}$: $\nu_{C=O}$ 1740 (ester). $\nu_{O-H}$ 3550 (—OH).

(3) Sodium (3.5 g.) was dissolved in methanol (60 ml.), and the above-obtained mixture (28.5 g.) was added to this solution. The resulting mixture was cooled to 10° C, followed by addition of water (3.5 ml.), and then left to stand overnight at 25° C.

After the removal of methanol by evaporation in vacuo, the residue was washed with diethyl ether, and then dissolved in water. The aqueous solution was acidified by addition of dilute hydrochloric acid, then gradually heated to evolve carbon dioxide, and further refluxed for 1.5 hours.

After cooling, the reaction mixture was extracted with diethyl ether. The diethyl ether extract was washed with dilute aqueous sodium carbonate solution, dried, and evaporated in vacuo to obtain a crude product of 2-[4-(2-methyl-3-hydroxybutyl)phenyl]propionaldehyde (18 g.), yield 82% (calculated from 4-(2-methyl-3-acetoxybutyl)phenyl methyl ketone).

Subsequently, the above-obtained product was purified by column chromatography (silica gel) to obtain the pure product (14.5 g.).

IR(neat) cm$^{-1}$: $\nu_{C=O}$ 1710 (aldehyde) $\nu_{O-H}$ 3420 (—OH) MS m/e: 220 (M$^+$), 173 (M$^+$ — (CHO + H$_2$O))

(4) An aqueous solution (20 ml.) containing AgNO$_3$ (5 g.), was added to an ethanol solution (200 ml.) containing 2-[4-(2-methyl-3-hydroxybutyl)phenyl] propionaldehyde (2.2 g.). In addition, N-sodium hydroxide solution (55 ml.) was added little by little with stirring.

After the mixture was stirred for 6 hours, it was filtered. Then the filtrate was concentrated by evaporation in vacuo, and washed with diethyl ether. Subsequently, the resulting material was acidified by addition of dilute hydrochloric acid, and extracted with diethyl ether. The diethyl ether extract was washed with water, dried, and evaporated in vacuo to obtain the crude product of 2-[4-(2-methyl-3-hydroxybutyl)phenyl]-propionic acid (1.9 g.), yield 80%.

The product was recrystallized from a mixed solvent consisting of diethyl ether and n-hexane to give pure crystals.

m.p. 85° – 88° C elemental analysis: (for C$_{14}$H$_{20}$O$_3$). Calcd.(%): C 71.16, H 8.53. Found (%): C 71.40, H 8.60.

IR(KBr) cm$^{-1}$: $\nu_{C=O}$ 1700 (—COOH). $\nu_{O-H}$ 3450 (—OH).

EXAMPLE 2

Preparation of 2-[4-(2-methyl-3-oxobutyl)-phenyl]propionic acid (1) Using (2-methyl-3-oxobutyl)benzene, the same operation as in Example 1 - (1) was repeated to obtain 4-(2-methyl-3-oxobutyl)phenyl methyl ketone.

b.p. 107° – 111° C / 0.15 mmHg IR(neat) cm$^{-1}$: $\nu_{C=O}$ 1670 (aromatic ketone). $\nu_{C=O}$ 1700 (aliphatic ketone).

(2) 4-(2-methyl-3-oxobutyl)phenyl methyl ketone (40.8 g.), ethylene glycol (20 g.) and p-toluenesulfonic acid (20 mg.) were mixed, and stirred at 25° C overnight. Then the water produced by the reaction was removed by evaporation in vacuo while keeping a temperature at 50° C for 3 hours.

After the reaction mixture was made basic with dilute aqueous sodium carbonate solution, it was extracted with diethyl ether. The diethyl ether extract was washed with water, dried, and freed of solvent by evaporation in vacuo. The resulting liquor was fractionated by vacuum distillation to obtain 4-(2-methyl-3-ethylenedioxybutyl)phenyl methyl ketone (30 g.), yield 60%.

IR(neat) cm$^{-1}$: $\nu_{C=O}$ 1670 (aromatic ketone)

Sodium methoxide (12 g.) was added to a mixture of 4-(2-methyl-3-ethylenedioxybutyl)phenyl methyl ketone (24.8 g.), methyl chloroacetate (21 g.) and n-hexane (80 ml.) with stirring in a stream of nitrogen at −5° to 0° C over a period of 1 hour. Subsequently, after the reaction temperature was raised to 25° C. for 1 hour, the mixture was stirred at 35° – 40° C for 3 hours.

Then the resulting mixture was poured into ice-water and extracted with diethyl ether. The diethyl ether extract was washed with water, dried, and then evaporated in vacuo to obtain a crude product of methyl 3-[4-(2-methyl-3-ethylenedioxybutyl)phenyl]-2,3-epoxybutanoate (30 g.), yield 98%.

IR(neat) cm$^{-1}$: $\nu_{C=O}$ 1740 (ester)

(4) Sodium (3 g.) was dissolved in methanol (60 ml.), and the above-obtained methyl 3-[4-(2-methyl-3-ethylenedioxybutyl)phenyl]-2,3 epoxybutanoate (30 g.) was added to this solution. The resulting mixture was cooled to 10° C, followed by addition of water (3 ml.), and then left to stand overnight at 25° C.

After the removal of methanol by evaporation in vacuo, the residue was washed with diethyl ether, and then dissolved in water. The aqueous solution was acidified by addition of dilute hydrochloric acid, then gradually heated to evolve carbon dioxide, and further refluxed for 1.5 hours.

After cooling, the reaction mixture was extracted with diethyl ether. The diethyl ether extract was washed with dilute aqueous sodium carbonate solution, dried, and evaporated in vacuo to obtain a crude product of 2-[4-(2-methyl-3-oxobutyl)phenyl]propionaldehyde (16.3 g.), yield 75% (calculated from 4-(2-methyl-3-ethylenedioxybutyl)phenyl methyl ketone). Subsequently, the above-obtained product was purified by column chromatography (silica gel) to obtain the pure product (9 g.).

IR(neat) cm$^{-1}$: $\nu_{C=O}$ 1710 MS m/e: 218 (M$^+$), 189 (M$^+$ − CHO)

(5) An aqueous solution (20 ml.) containing AgNO$_3$ (5 g.), was added to an ethanol solution (200 ml.) containing 2-[4-(2-methyl-3-oxobutyl)phenyl] propionaldehyde (2.2 g.). In addition, N-sodium hydroxide (55 ml.) was added little by little with stirring.

After the mixture was stirred for 6 hours, it was filtered. Then the filtrate was concentrated by evaporation in vacuo and washed with diethyl ether. Subsequently, the resulting material was acidified by addition of dilute hydrochloric acid, and extracted with diethyl ether. The ether extract was washed with water, dried, and evaporated in vacuo to obtain the crude product of 2-[4-(2-methyl-3-oxobutyl)phenyl]propionic acid (1.9 g.), yield 80%.

The product was purified by column chromatography (silica gel) to obtain a pure oil (1.4 g.).

IR(neat) cm$^{-1}$: $\nu_{C=O}$ 1690 (—COOH, <CO)

EXAMPLE 3

Preparation of 2-[4-(2-ethyl-3-hydroxybutyl-phenyl]propionic acid (1) Using (2-ethyl-3-acetoxybutyl)benzene, the same operation as in Example 1 - (1) was repeated to obtain 4-(2-ethyl-3-acetoxybutyl)phenyl methyl ketone.

b.p. 118° – 123° C / 0.15 mmHg IR(neat) cm$^{-1}$: $\nu_{C=O}$ 1670 (aromatic ketone) $\nu_{C=O}$ 1720 (ester)

(2) Using 4-(2-ethyl-3-acetoxybutyl)phenyl methyl ketone obtained above, the same operations as in Example 1 - (2) and (3) were repeated to obtain 2-[4-(2-ethyl-3-hydroxybutyl)phenyl]propionaldehyde.

IR(neat) cm$^{-1}$: $\nu_{C=O}$ 1710 (aldehyde) $\nu_{O-H}$ 3420 (—OH) MS m/e: 234 (M+), 187 (M+ — (CHO + H$_2$O))

(3) An aqueous solution (20 ml.) containing AgNO$_3$ (5 g.), was added to an ethanol solution (200 ml.) containing 2-[4-(2-ethyl-3-hydroxybutyl)phenyl] propionaldehyde (2.3 g.). In addition, N-sodium hydroxide solution (55 ml.) was added little by little with stirring.

After the mixture was stirred for 6 hours, it was filtered. Then the filtrate was concentrated by evaporation in vacuo and washed with diethyl ether. Subsequently, the resulting material was acidified by addition of dilute hydrochloric acid, and extracted with diethyl ether. The diethyl ether extract was washed with water, dried, and evaporated in vacuo to obtain the crude product of 2-[4-(2-ethyl-3-hydroxybutyl)phenyl]propionic acid (2 g.), yield 80%.

The product was recrystallized from a mixed solvent consisting of diethyl ether and n-hexane to give pure crystals.

m.p. 100° – 103° C elemental analysis: (for C$_{15}$H$_{22}$O$_3$) Calcd.(%): C 71.97, H 8.86 Found (%): C 71.79, H 8.89 IR(KBr) cm$^{-1}$: $\nu_{C=O}$ 1700 (—COOH) $\nu_{O-H}$ 3450 (—OH)

EXAMPLE 4

Preparation of 2-[4-(2-ethyl-3-oxobutyl)phenyl]propionic acid (1) Using (2-ethyl-3-oxobutyl)benzene, the same operation as in Example 1 - (1) was repeated to obtain 4-(2-ethyl-3-oxobutyl)phenyl methyl ketone.

b.p. 111° – 116° C / 0.15 mmHg IR(neat) cm$^{-1}$: $\nu_{C=O}$ 1670 (aromatic ketone) $\nu_{C=O}$ 1700 (aliphatic ketone)

(2) Using 4-(2-ethyl-3-oxobutyl)phenyl methyl ketone obtained above, the same operation as in Example 2 - (2) was repeated to obtain 4-(2-ethyl-3-ethylenedioxybutyl)phenyl methyl ketone.

b.p. 115° – 123° C / 0.1 mmHg IR(neat) cm$^{-1}$: $\nu_{C=O}$ 1670 (aromatic ketone)

(3) Using 4-(2-ethyl-3-ethylenedioxybutyl)phenyl methyl ketone obtained above, the same operations as in Example 2 - (3) and (4) were repeated to obtain 2-[4-(2-ethyl-3-oxobutyl)phenyl]propionaldehyde.

IR(neat) cm$^{-1}$: $\nu_{C=O}$ 1710

MS m/e: 232 (M+), 203

(4) An aqueous solution (20 ml.) containing AgNO$_3$ (5 g.), was added to an ethanol solution (200 ml.) containing 2-[4-(2-ethyl-3-oxobutyl)phenyl]propionaldehyde (2.3 g.). In addition, N-sodium hydroxide solution (55 ml.) was added little by little with stirring.

After the mixture was stirred for 6 hours, it was filtered. Then the filtrate was concentrated by evaporation in vacuo and washed with diethyl ether. Subsequently, the resulting material was acidified by addition of dilute hydrochloric acid, and extracted with diethyl ether. The diethyl ether extract was washed with water, dried, and evaporated in vacuo to obtain the crude product of 2-[4-(2-ethyl-3-oxobutyl)phenyl]propionic acid (2 g.), yield 80%.

Subsequently, the product was purified by column chromatography (silica gel) to obtain a pure oil (1.6 g.).

IR(neat) cm$^{-1}$: $\nu_{C=O}$ 1690 (—COOH, <CO)

What is claimed is:

1. A compound represented by the general formula:

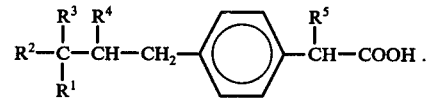

wherein R$^1$ represents hydrogen; R$^2$ represents hydroxy; R$^3$ represents lower alkyl; R$^4$ represents hydrogen or lower alkyl; and R$^5$ represents lower alkyl; wherein lower alkyl has 1 – 5 carbon atoms; or a non-toxic salt thereof.

2. A compound according to claim 1 wherein R$^3$ is methyl, R$^4$ is methyl or ethyl, and R$^5$ is methyl.

3. The compound according to claim 1 which is 2-[4-(2-ethyl-3-hydroxybutyl)phenyl]propionic acid or its non-toxic salt.

4. The compound of claim 1, in which R$^3$ and R$^5$ are methyl groups.

5. The compound of claim 1, in which R$^3$ and R$^5$ are methyl groups, and R$^4$ is a methyl or ethyl group.

6. The compound of claim 1 wherein R$^1$ represents a hydrogen atom and R$^2$ represents a hydroxy group.

7. The compound of claim 1 wherein R$^3$ is methyl, R$^4$ is ethyl, and R$^5$ is methyl.

8. The compound of claim 1 wherein R$^3$ is methyl, R$^4$ is methyl, and R$^5$ is methyl.

* * * * *